(12) United States Patent
Williams

(10) Patent No.: US 10,779,846 B2
(45) Date of Patent: Sep. 22, 2020

(54) SURGICAL CLAMPING DEVICE WITH PARALLEL CLOSURE

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 150 days.

(21) Appl. No.: 16/120,520

(22) Filed: Sep. 4, 2018

(65) Prior Publication Data
US 2019/0133630 A1 May 9, 2019

Related U.S. Application Data

(60) Provisional application No. 62/581,064, filed on Nov. 3, 2017.

(51) Int. Cl.
*A61B 17/29* (2006.01)
*A61B 5/022* (2006.01)
(Continued)

(52) U.S. Cl.
CPC .......... *A61B 17/29* (2013.01); *A61B 5/02233* (2013.01); *A61B 5/02241* (2013.01); (Continued)

(58) Field of Classification Search
CPC ..... A61B 17/29; A61B 17/128; A61B 17/122; A61B 2017/2912; A61B 2017/2913; (Continued)

(56) References Cited

U.S. PATENT DOCUMENTS 4,887,612 A * 12/1989 Esser .................... A61B 10/06
600/564
6,716,232 B1 4/2004 Vidal et al.
(Continued)

FOREIGN PATENT DOCUMENTS

EP 0503662 A1 9/1992
EP 1545332 B1 8/2007
(Continued)

OTHER PUBLICATIONS

European Search Report dated May 16, 2019, issued in EP Appln. No. 19152122.
(Continued)

*Primary Examiner* — Ashley L Fishback
(74) *Attorney, Agent, or Firm* — Carter, DeLuca & Farrell LLP

(57) ABSTRACT

A surgical clamping device includes a handgrip, an actuation assembly, an elongated body portion, an upper jaw assembly, and a lower jaw assembly. Each of the upper and lower jaw assemblies includes and an elongated jaw body and a distal clamping portion that is supported on a distal end of a respective elongated jaw body. Each of the elongated jaw bodies includes a proximal end that is pivotally connected to the actuation assembly by a pivot member located within the handgrip. The pivot member is spaced from the distal clamping portions of the upper and lower jaw assemblies such that the distal clamping portions of the upper and lower jaw assemblies remain substantially parallel as the upper and lower jaw assemblies are pivoted between open and clamped positions.

19 Claims, 17 Drawing Sheets

(51) Int. Cl.
*A61B 17/072* (2006.01)
*A61B 17/00* (2006.01)
*A61B 90/00* (2016.01)
*A61B 17/28* (2006.01)
*A61B 17/122* (2006.01)
*A61B 17/12* (2006.01)

(52) U.S. Cl.
CPC ... *A61B 17/122* (2013.01); *A61B 2017/00017* (2013.01); *A61B 2017/00022* (2013.01); *A61B 2017/00557* (2013.01); *A61B 2017/07214* (2013.01); *A61B 2017/12004* (2013.01); *A61B 2017/2808* (2013.01); *A61B 2017/2825* (2013.01); *A61B 2017/2912* (2013.01); *A61B 2017/2936* (2013.01); *A61B 2017/2939* (2013.01); *A61B 2017/2944* (2013.01); *A61B 2017/2947* (2013.01); *A61B 2090/065* (2016.02); *A61B 2505/05* (2013.01)

(58) Field of Classification Search
CPC .... A61B 2017/2915; A61B 2017/2916; A61B 2017/2932; A61B 2017/2933; A61B 2017/2936; A61B 2017/2939; A61B 2017/2944; A61B 2017/2934; A61B 2090/065

See application file for complete search history.

(56) References Cited

U.S. PATENT DOCUMENTS

| | | |
|---|---|---|
| 7,252,666 B2 | 8/2007 | Dycus |
| 7,617,961 B2 | 11/2009 | Viola |
| 8,403,197 B2 | 3/2013 | Vidal et al. |
| 8,616,427 B2 | 12/2013 | Viola |
| 2007/0027469 A1 | 2/2007 | Smith et al. |
| 2014/0336677 A1 | 11/2014 | Hessler |
| 2015/0272569 A1* | 10/2015 | Leimbach ........... H01M 10/425 227/175.1 |
| 2016/0296233 A1* | 10/2016 | Wheeler ................ A61B 17/10 |
| 2018/0317914 A1 | 11/2018 | Badawi |

FOREIGN PATENT DOCUMENTS

| | | |
|---|---|---|
| EP | 3192455 A1 | 7/2017 |
| WO | 03030743 A2 | 4/2003 |

OTHER PUBLICATIONS

International Search Report dated Mar. 12, 2019, issued in PCT/US2018/057481.

\* cited by examiner

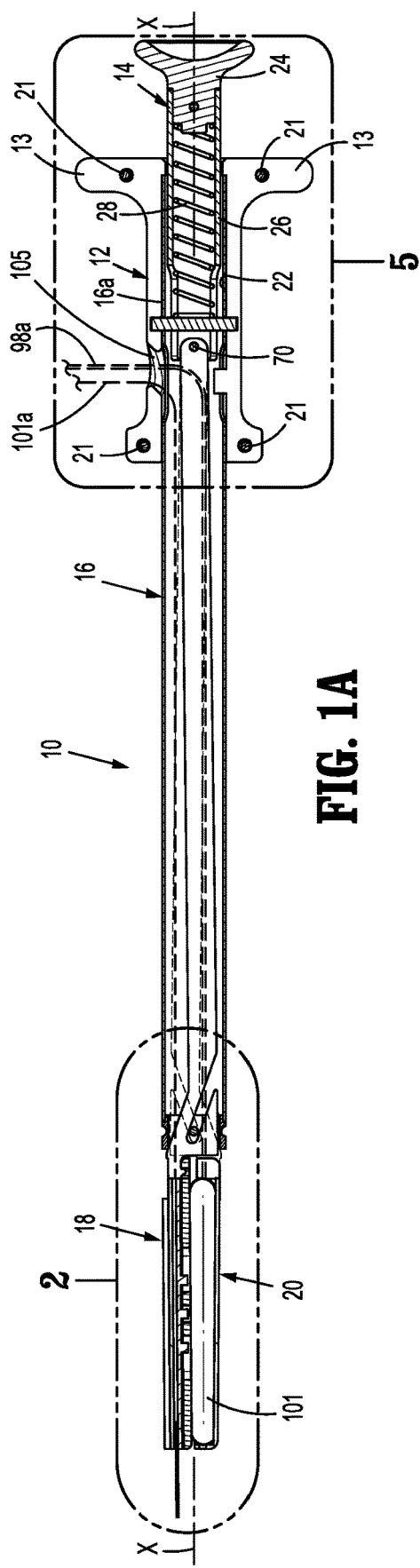
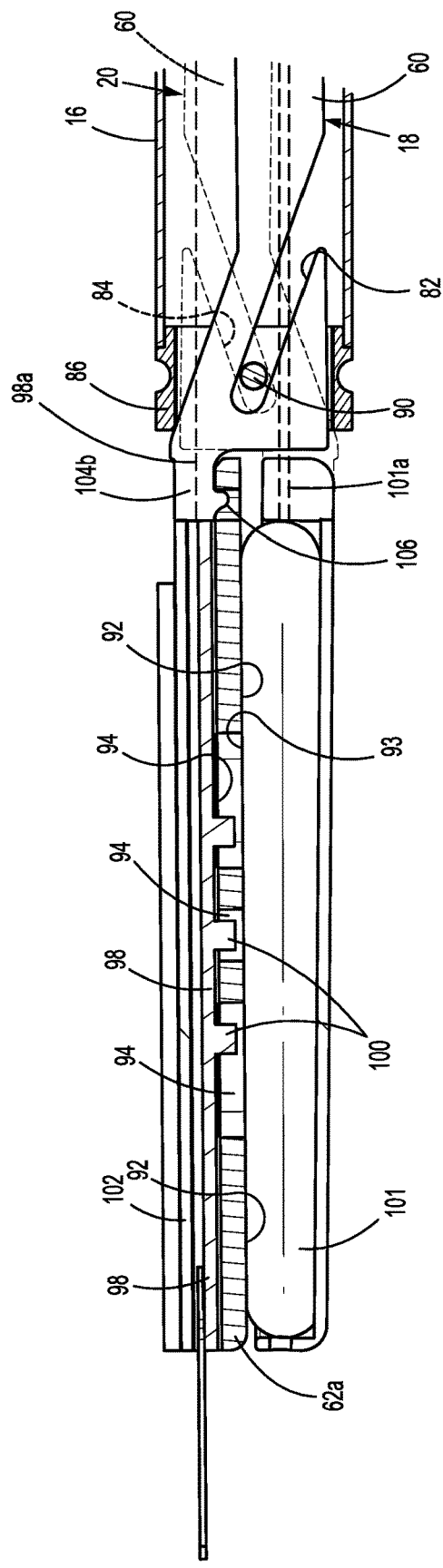
FIG. 1A
FIG. 2

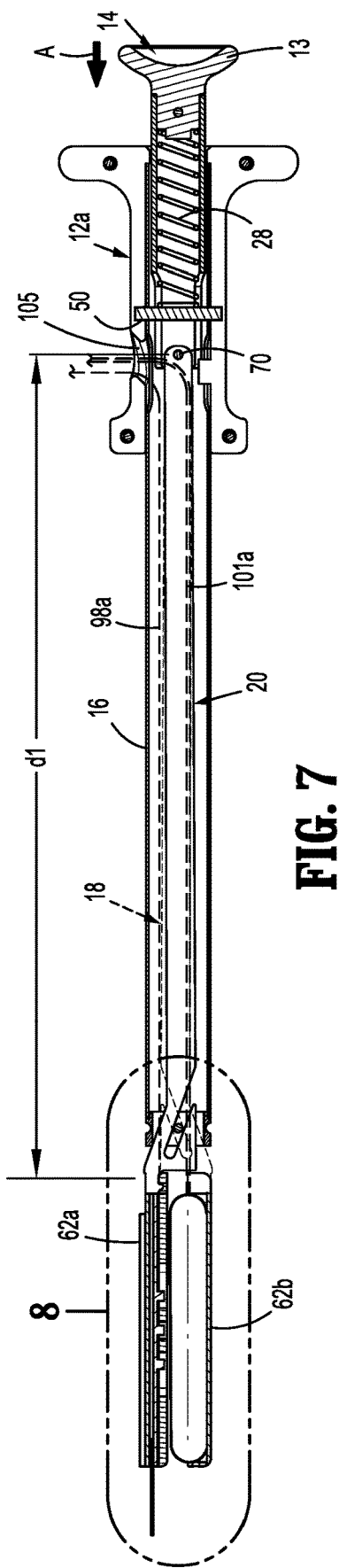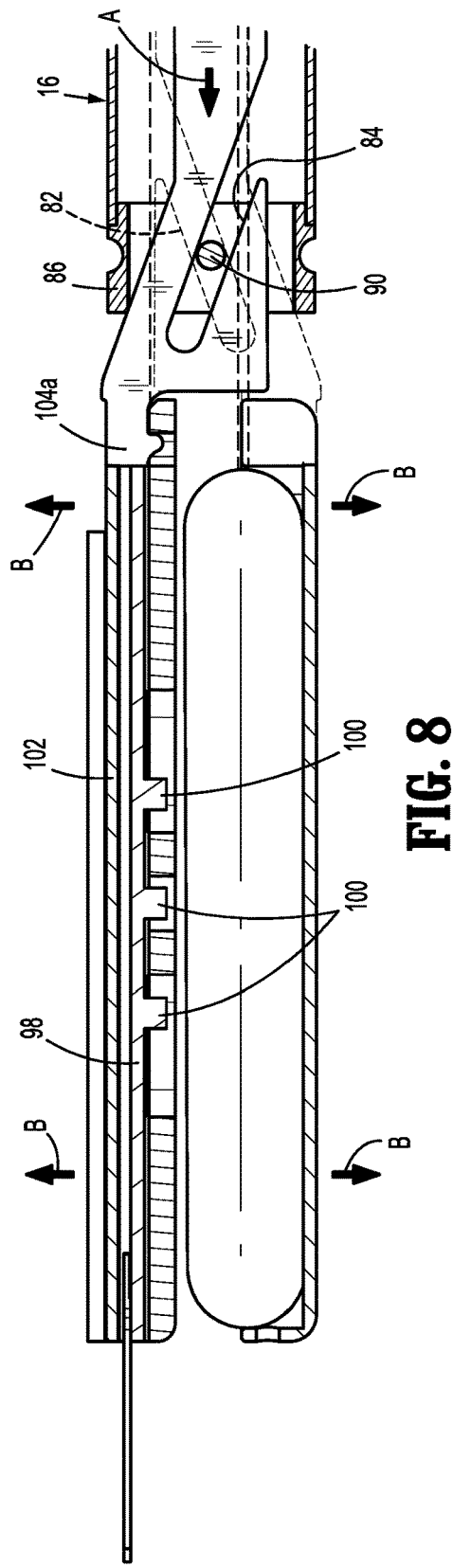

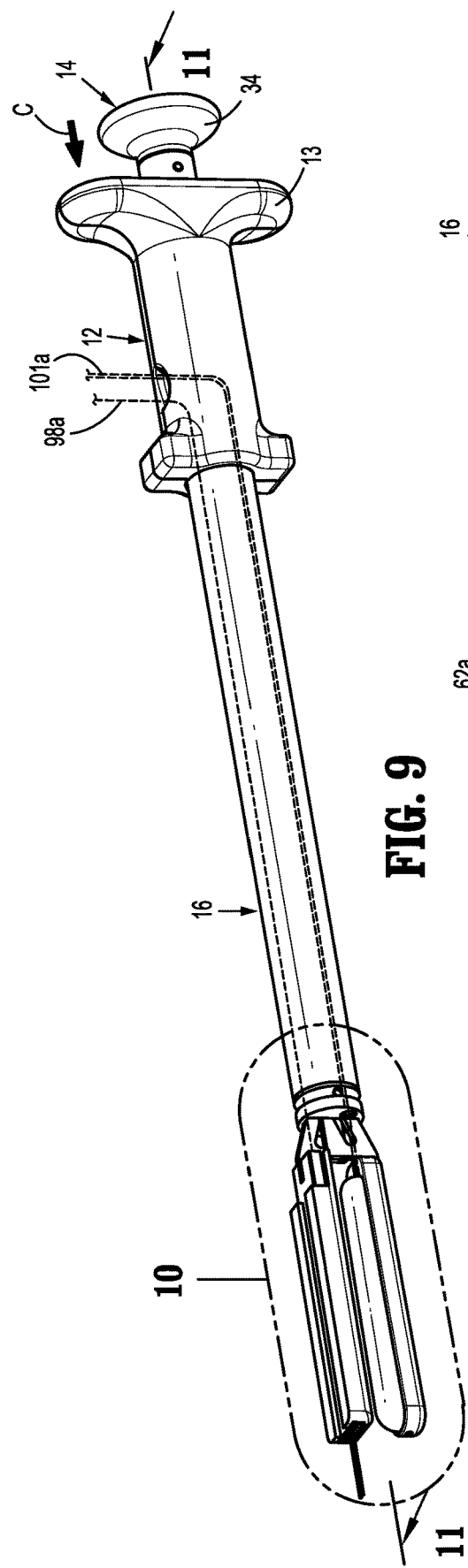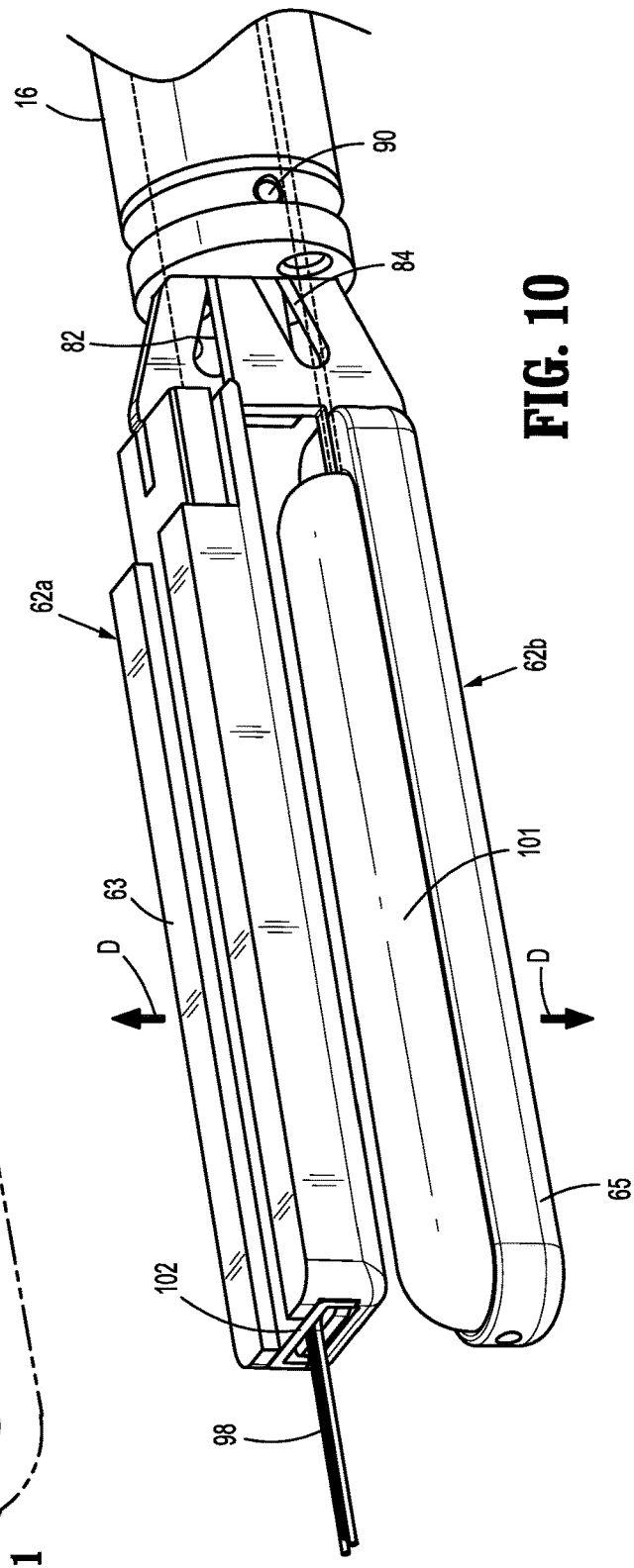

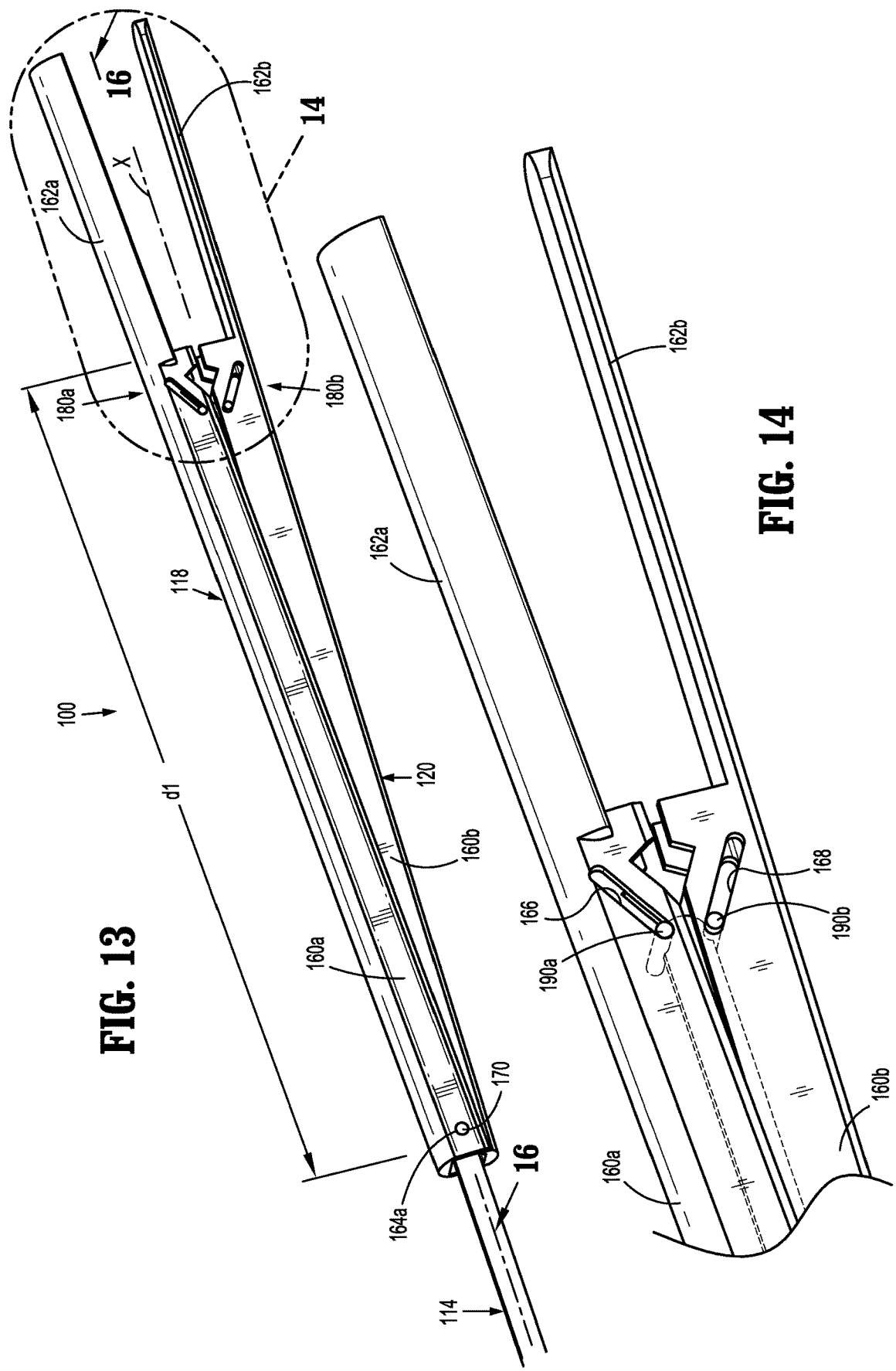

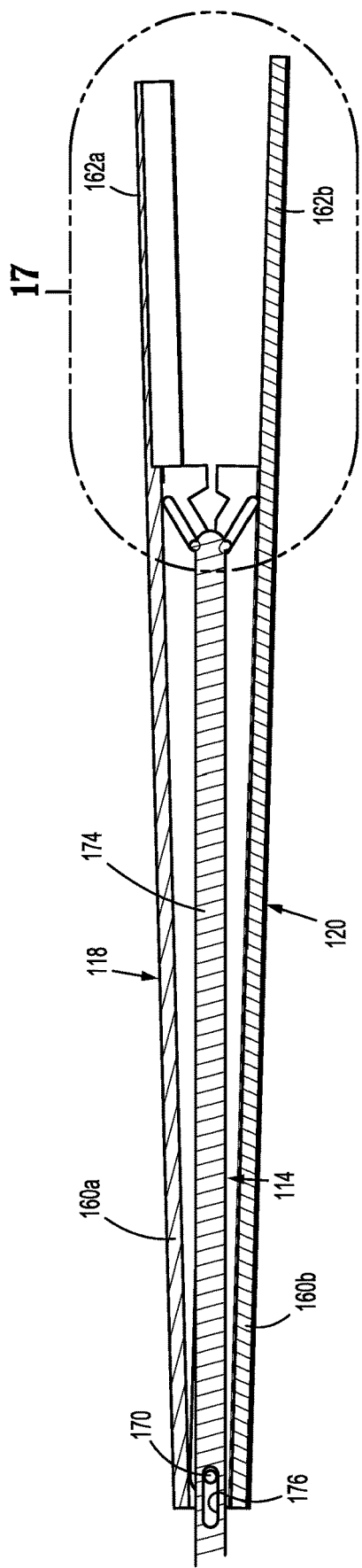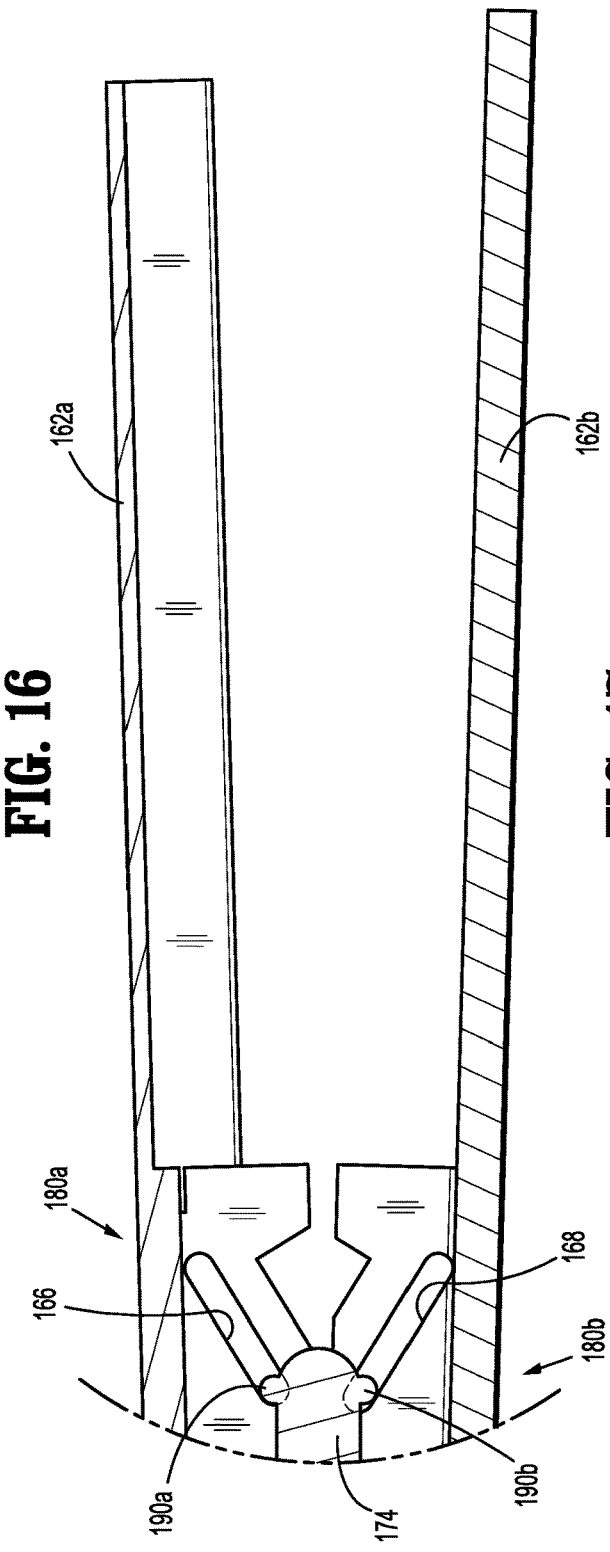
FIG. 16
FIG. 17

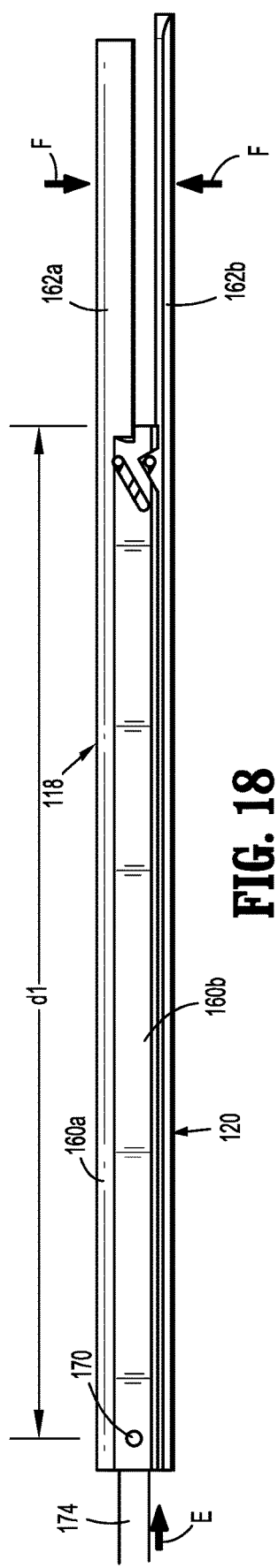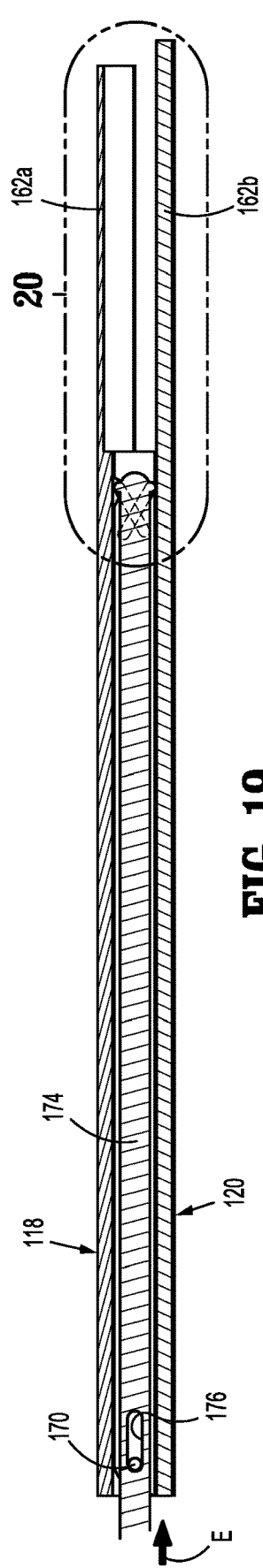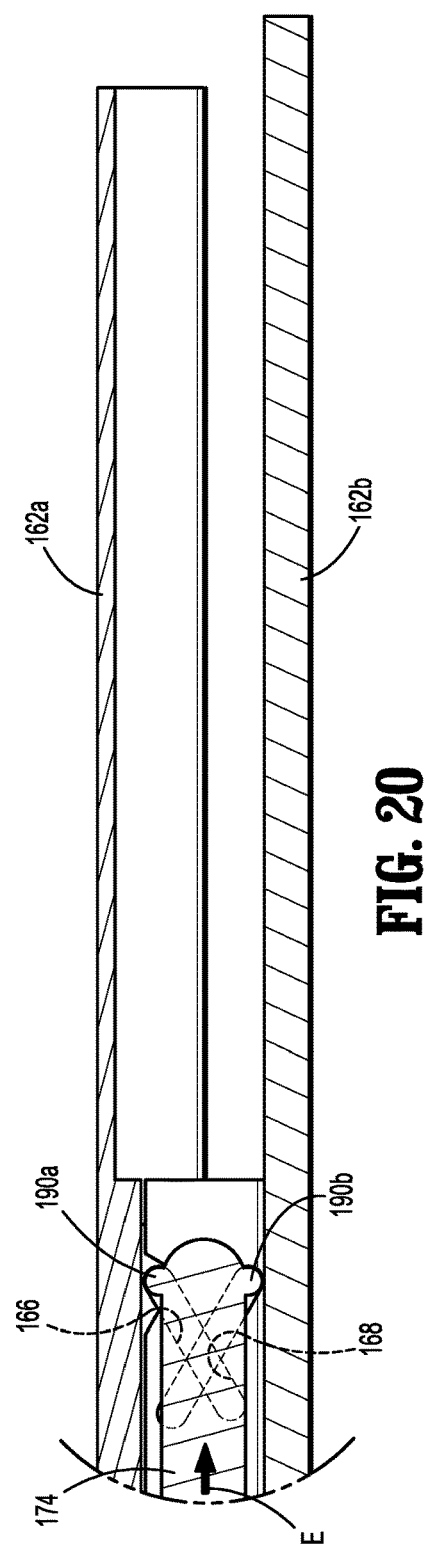

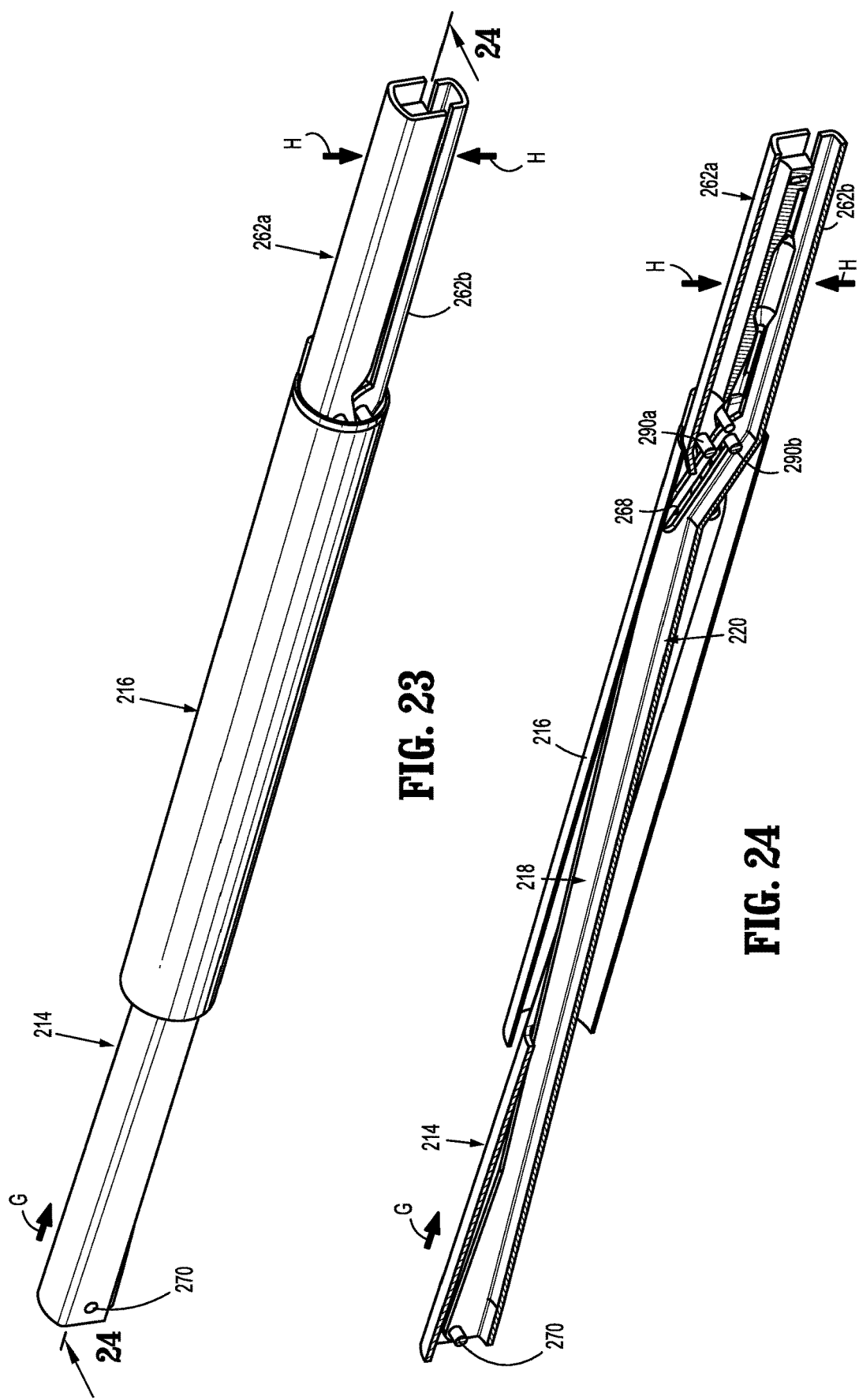

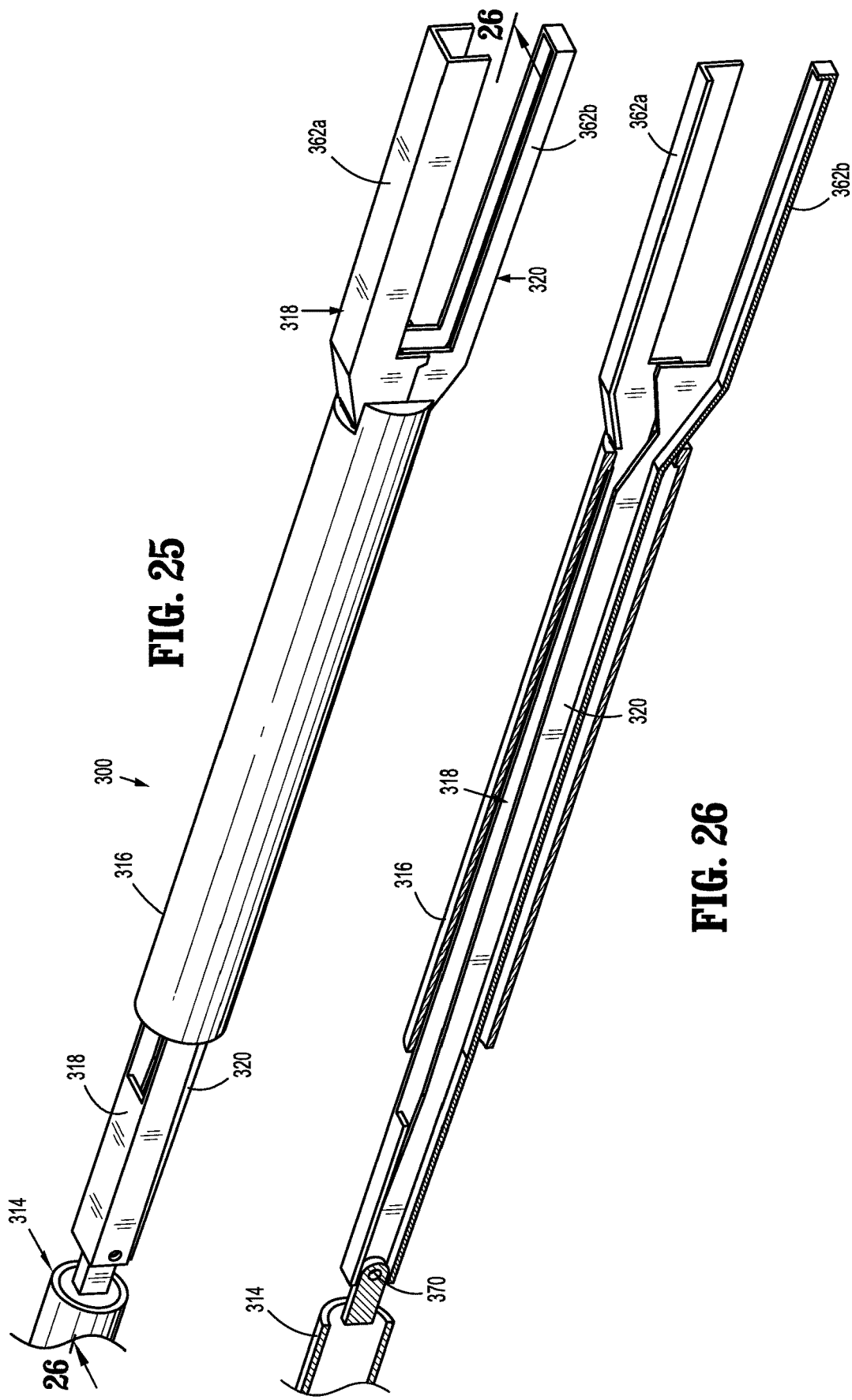

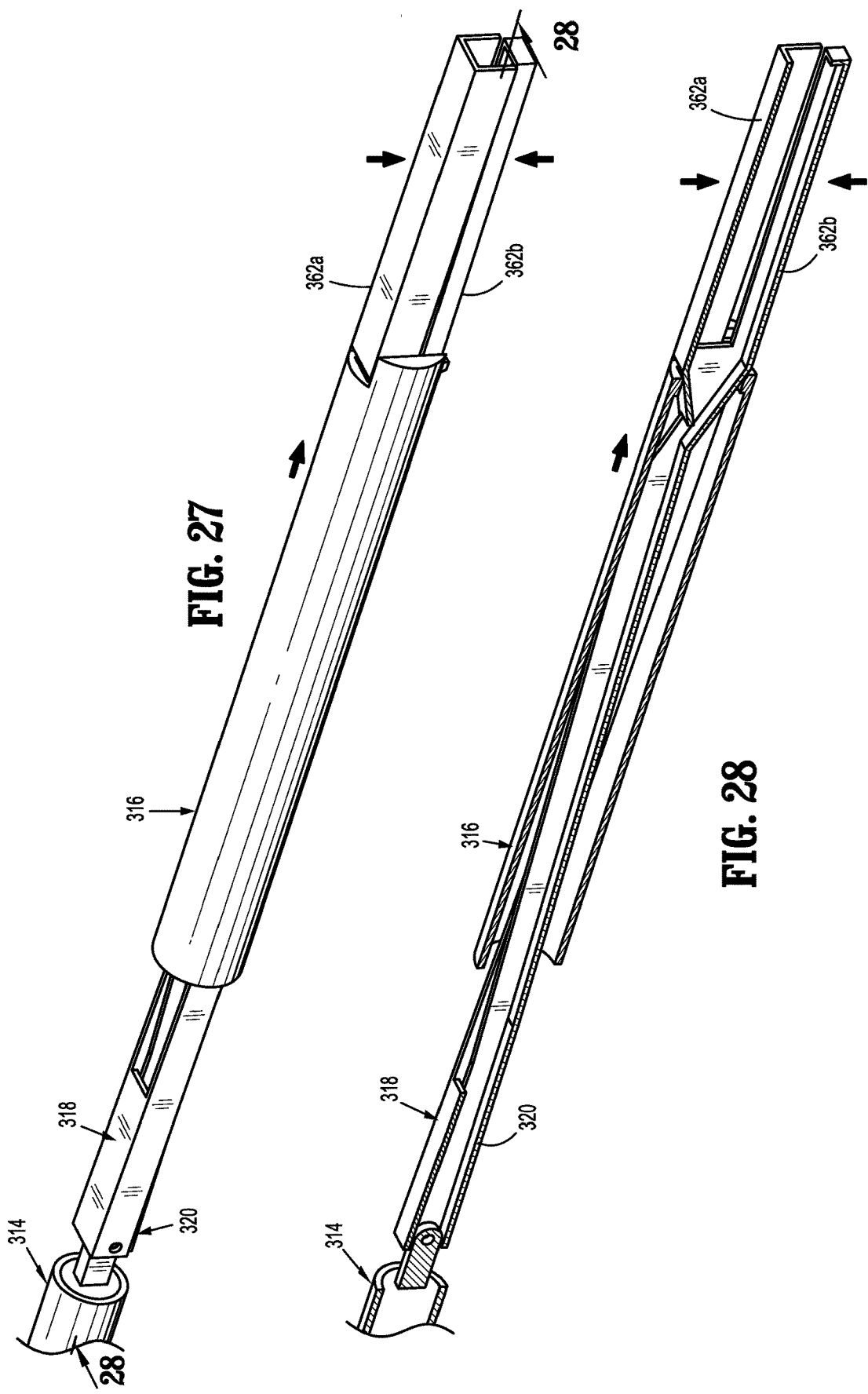

SURGICAL CLAMPING DEVICE WITH PARALLEL CLOSURE

CROSS-REFERENCE TO RELATED APPLICATION

This application claims the benefit of and priority to U.S. Provisional Patent Application No. 62/581,064 filed Nov. 3, 2017, the entire disclosure of which is incorporated by reference herein.

BACKGROUND

1. Technical Description

The present disclosure is directed to surgical clamping or grasping devices and, more particularly, to surgical clamping or grasping devices with jaws that have distal clamping portions that are substantially parallel to each other during movement between open and clamped positions.

2. Background of Related Art

Surgical clamping devices for clamping tissue are well known in the art. These devices include vascular clamping devices which are used to occlude blood flow through vasculature. Typically, surgical clamping devices include a pair of jaws that are movable in relation to each other to clamp tissue positioned between the jaws. In some devices, the jaws are pivotally coupled to each other or to support structure at their proximal ends and are pivotal from an open position to a clamped position. In such embodiments, movement of the jaws from the open position to the clamped position tends to urge or extrude tissue from between the jaws during closure which results in uneven pressure distribution on the tissue.

In other known devices that clamp tissue between a pair of jaws such as surgical staplers, a mechanism is provided to effect parallel closure of the jaws to improve pressure distribution on tissue and to limit tissue extrusion from between the jaws during clamping of tissue. The mechanism may include spaced screws which support opposite ends of one or both of the jaw. The screws can be rotated to effect parallel closure of the jaws. Although these devices minimize tissue extrusion and provide a more uniform pressure distribution on tissue, the devices can be overly complex and provide limited access to the clamping surfaces of the jaws in the open position of the jaws.

Accordingly, a continuing need exists in the art for a tissue clamping device that is simple in construction yet provides the benefits of parallel closure.

SUMMARY

One aspect of the present disclosure is directed to a surgical clamping device including a hand grip, and actuator assembly, an elongated body and, upper and lower jaw assemblies. The actuator assembly is supported by the hand grip and is movable in relation to the hand grip between retracted and advanced positions. The elongated body is supported on and extends distally from the hand grip. The elongated body defines a longitudinal axis and supports a cam member. The upper and lower jaw assemblies each include an elongate jaw body and a distal clamping portion having a cam surface. Each of the elongate jaw bodies extends from the hand grip through the elongated body and includes a proximal portion pivotally secured to the actuator within the hand grip about a pivot member. The actuator is movable between a retracted position and an advanced position to move the cam surfaces of the distal clamping portions in relation to the cam member of the elongated body to pivot the upper and lower jaw assemblies in relation to each other between an open position and a clamped position. The actuator assembly includes a biasing member positioned to urge the upper and lower jaw assemblies towards the clamped position.

In embodiments, a bushing defining a transverse slot is supported on a distal end of the elongated body and supports the cam member. The upper and lower jaw assemblies extend through the transverse slot.

In some embodiments, each of the upper and lower jaw assemblies includes a central cam portion that defines a cam slot that receives the cam member.

In certain embodiments, a fluid flow sensor is supported on one of the upper and lower jaw assemblies. The fluid flow sensor is provided to identify fluid flow within a vessel clamped between the distal clamping portions of the upper and lower jaw assemblies.

In embodiments, the other one of the upper and lower jaws supports an inflatable bladder, wherein the inflatable bladder and the sensor are positioned such that in the clamped position tissue is clamped between the sensor and the inflatable bladder.

In some embodiments, the presently disclosed clamping device includes a controller that is configured to facilitate inflatation of the inflatable bladder and actuation of the sensor.

In embodiments, the cam member includes first and second cam members. Each of the first and second cam members is positioned within one of the cam slots of the upper and lower jaw assemblies.

In some embodiments, the upper and lower jaw assemblies are axially movable in relation to the elongate body.

In certain embodiments, the upper and lower jaw assemblies are axially fixed in relation to the elongate body.

In embodiments, the hand grip defines a through bore and the actuator assembly is movably supported within the through bore.

In some embodiments, the actuator assembly includes an actuator knob, an actuator body, and a biasing member. The actuator knob is supported on a proximal portion of the actuator body and extends from a proximal end of the hand grip.

In certain embodiments, the actuator body is tubular and the biasing member includes a coil spring positioned within the actuator body.

In embodiments, a cross-pin is fixedly supported within the through bore of the hand grip. The cross-pin extends through the actuator body and engages a distal end of the coil spring.

In some embodiments, the actuator body defines spaced longitudinally extending cut outs and the cross-pin being is positioned within the longitudinally extending cut outs such that the actuator body is axially moveable in relation to the hand grip and the cross-pin.

In certain embodiments, the pivot member is spaced from a proximal end of the distal clamping portions by a distance d, wherein d is greater than 4.5 inches.

In embodiments, the pivot member is spaced from a proximal end of the distal clamping portions by a distance d, wherein d is between 4.5 inches and 7.5 inches.

In embodiments, the pivot member is spaced from a proximal end of the distal clamping portions by a distance d, wherein d is 6 inches.

In embodiments, each of the upper and lower jaw assemblies includes a central cam portion that defines an outer cam surface, the outer cam surfaces being positioned to engage a distal end of the elongated body to effect movement of the upper and lower jaw assemblies to the clamped position.

BRIEF DESCRIPTION OF THE DRAWINGS

Various embodiments of the presently disclosed surgical clamping device are described herein below with reference to the drawings, wherein:

FIG. 1A is a side cross-sectional view taken along section line 1A;

FIG. 2 is an enlarged view of the indicated area of detail shown in FIG. 1A;

FIG. 7 is a side cross-sectional view taken along section line 7-7 of FIG. 6;

FIG. 8 is an enlarged view of the indicated area of detail shown in FIG. 7;

FIG. 9 is a side perspective view of the surgical clamping device shown in FIG. 1 with jaws in an open position;

FIG. 10 is an enlarged view of the indicated area of detail shown in FIG. 9;

FIG. 13 is a side perspective view of another embodiment of the jaws and actuator of the presently disclosed surgical clamping device shown in FIG. 1 with the jaws in the open position;

FIG. 14 is an enlarged view of the indicated area of detail shown in FIG. 13;

FIG. 16 is a side cross-sectional view taken along section line 16-16 of FIG. 13;

FIG. 17 is an enlarged view of the indicated area of detail shown in FIG. 17;

FIG. 18 is a side perspective view of the jaws and actuator shown in FIG. 13 with the jaws in the closed position;

FIG. 19 is a side cross-sectional view taken along section lines 19-19 of FIG. 18;

FIG. 20 is an enlarged view of the indicated area of detail shown in FIG. 19;

FIG. 23 is a side perspective view of the jaws and actuator shown in FIG. 21 with the jaws in the closed position;

FIG. 24 is a cross-sectional view taken along section lines 24-24 of FIG. 23;

FIG. 25 is a side perspective view of yet another embodiment of the jaws and actuator of the presently disclosed surgical clamping device shown in FIG. 1 with the jaws in the open position;

FIG. 26 is a cross-sectional view taken along section lines 26-26 of FIG. 21;

FIG. 27 is a side perspective view of the jaws and actuator shown in FIG. 25 with the jaws in the closed position; and FIG. 28 is a cross-sectional view taken along section lines 28-28 of FIG. 27.

DETAILED DESCRIPTION OF EMBODIMENTS

Figure 1:
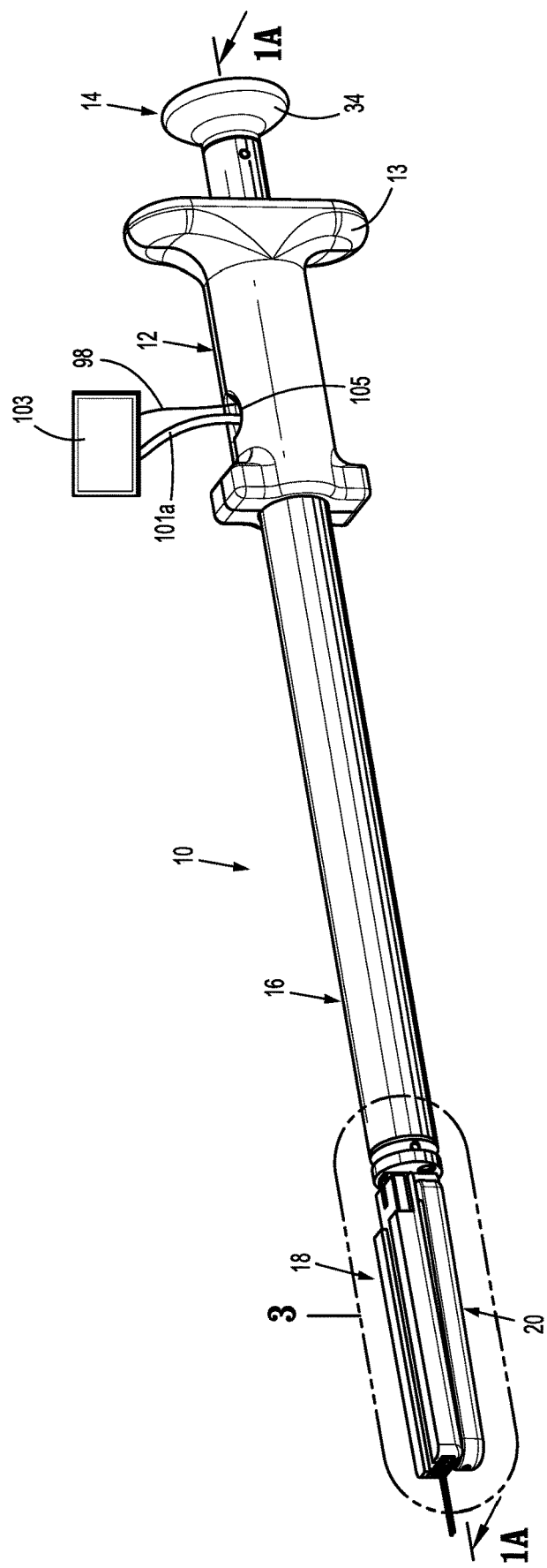
FIG. 1 is a side perspective view of an exemplary embodiment of the presently disclosed surgical clamping device with jaws in a closed position.

The presently disclosed surgical clamping device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

The presently disclosed surgical clamping device includes a handgrip, an actuation assembly, an elongated body portion, an upper jaw assembly, and a lower jaw assembly. Each of the upper and lower jaw assemblies includes an elongated jaw body and a distal clamping portion fixedly supported on the elongated jaw body. Each of the elongated jaw bodies of the upper and lower jaw assemblies includes a proximal end that is pivotally connected to the actuation assembly by a pivot member located adjacent the handgrip. The pivot member is spaced from the distal clamping portions of the upper and lower jaw assemblies and facilitates pivotal movement of the distal clamping portions of the upper and lower jaw assemblies between open and clamped positions. Because of the large spacing between the distal clamping portions of the upper and lower jaw assemblies and the pivot member, the distal clamping portions of the upper and lower jaw assemblies remain substantially parallel to each other during movement of the distal clamping portions between open and clamped positions.

Referring to FIGS. 1-5, the presently disclosed surgical clamping device shown generally as 10 includes a hand grip 12, an actuator assembly 14, an elongated body 16 defining a longitudinal axis "X", and upper and lower jaw assemblies 18 and 20, respectively. In embodiments, the hand grip 12 is formed from molded half-sections 12a, 12b that are secured together using screws 21 and together define a through bore 22 that receives a proximal portion of the elongated body 16. Alternately, the hand grip half-sections 12a, 12b can be secured together using any known fastening technique including welding, adhesives, or the like. The hand grip 12 has a proximal portion 13 that extends radially outwardly from the longitudinal axis "X" and facilitates gripping by a clinician as discussed in further detail below.

The elongated body 16 is tubular and has a proximal end that is positioned within the through bore 22 of the hand grip 12 and a distal portion that is spaced distally of the hand grip 12. The upper and lower jaw assemblies 18 and 20, respectively, are positioned within the elongated body 16 and extend from within the hand grip 12 to a position beyond the distal end of the elongated body 16.

Figure 4:
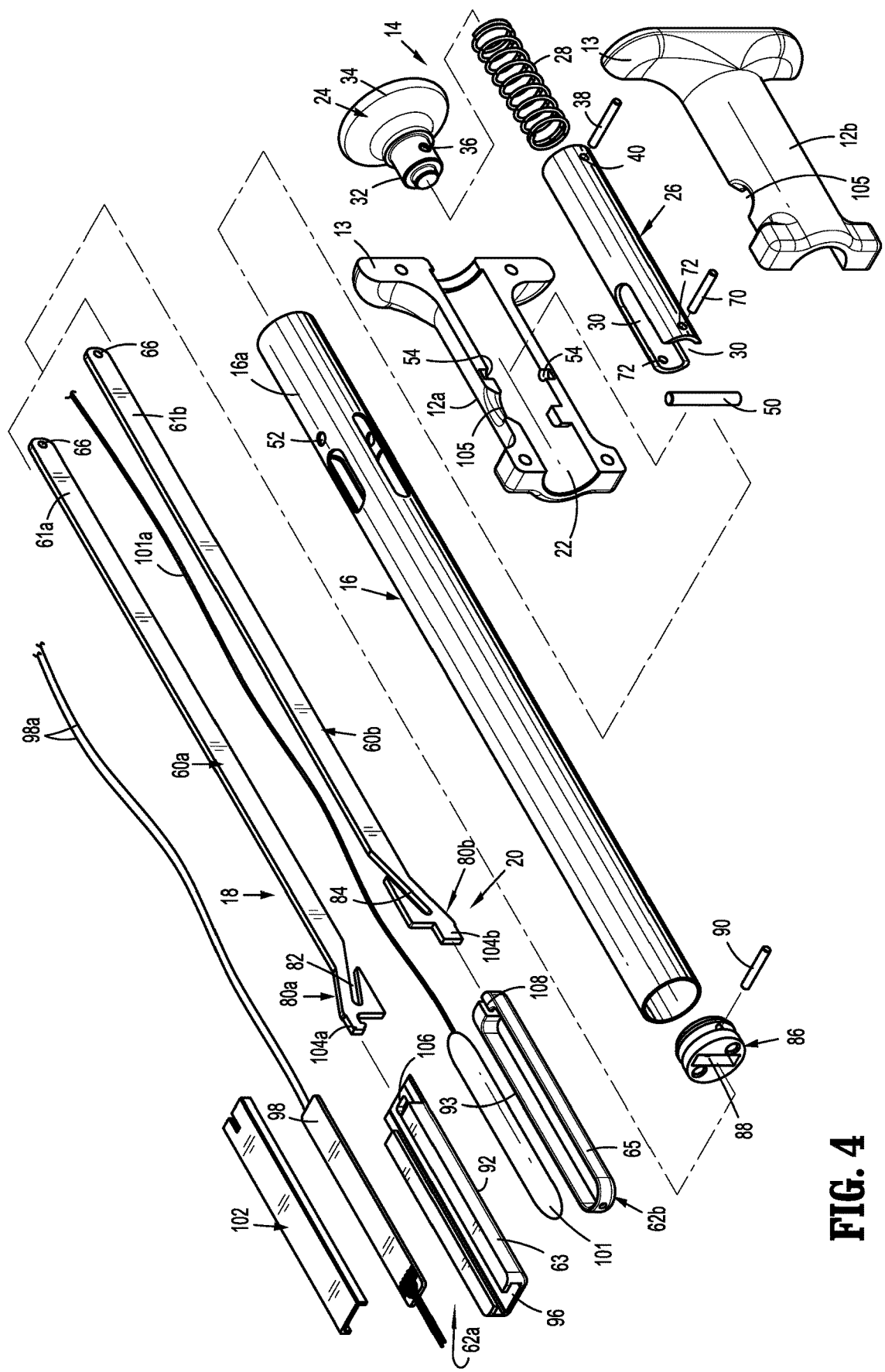
FIG. 4 is an exploded view of the surgical clamping device shown in FIG. 1.
Figure 5:
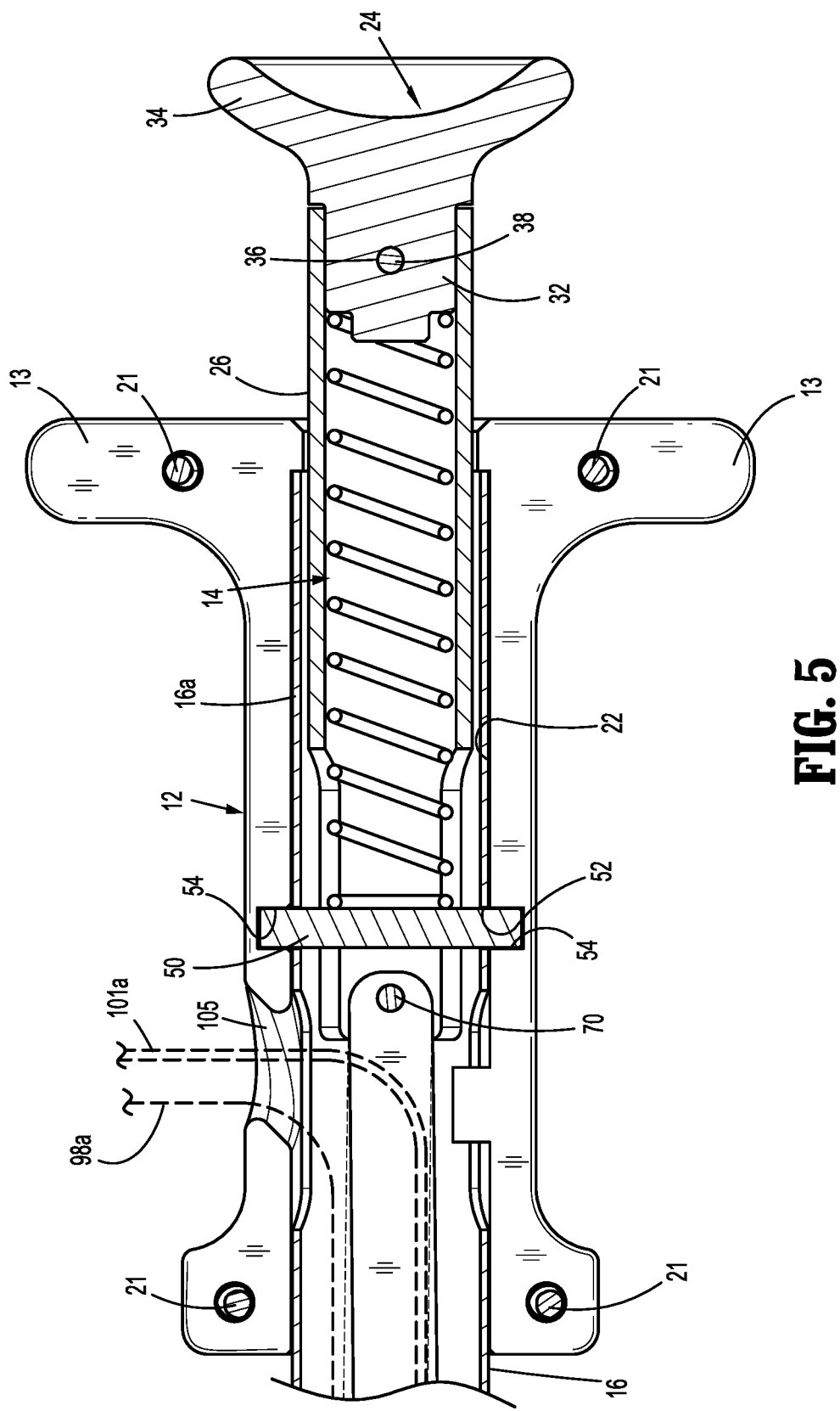
FIG. 5 is an enlarged view of the indicated area of detail shown in FIG. 1.

Referring to FIGS. 4 and 5, the actuator assembly 14 is supported within the through bore 22 of the hand grip 12 and within the elongated body 16 and includes an actuator knob 24, an actuator body 26, and a biasing member, e.g., coil spring 28. The actuator body 26 is tubular and is moveable within the through bore 22 of the hand grip 12 and a proximal portion 16a of the elongated body 16 from a retracted position to an advanced position. The actuator body 26 includes a distal portion that defines a pair of longitudinal cut outs 30 (FIG. 4). The actuator knob 24 includes a distal portion 32 that is received within a proximal portion of the actuator body 26 and a proximal, radially extending portion 34 that is configured to be engaged by the hand of a clinician. The distal portion 32 of the actuator knob 24 defines a bore 36 for receiving a pin 38. The pin 38 extends through openings 40 in the proximal portion of the actuator body 26 and the bore 36 in the actuator knob 24 to fixedly secure the actuator knob 24 to the actuator body 26. The actuator body 26 is secured within the proximal portion 16a of the elongated body 16 within the through bore 22 of the hand grip 12.

The proximal portion 16a of the elongated body 16 is secured within the through bore 22 of the hand grip 12 by a cross pin 50 (FIG. 5). The cross pin 50 extends through openings 52 in the elongated body 16, through the cut outs 30 in the actuator body 26, and into bores 54 defined within the hand grip 12 to axially secure the elongated body 16 to the hand grip 12. Since the cross pin 50 is positioned through the cut outs 30 in the actuator body 26, the actuator body 26, although rotatably fixed within the handgrip 12, can move axially in relation to the cross pin 50, the elongate body 16 and the hand grip 12. The spring 28 is positioned within the actuator body 26 between the actuator knob 24 and the cross pin 50 to urge the actuator body 26 proximally to a retracted position within the through bore 22 of the hand grip 12.

Referring to FIGS. 1-4, the upper and lower jaw assemblies 18 and 20 extend within the through bore 22 of the hand grip 12 through the elongate body 16 to a position distally of the elongate body 16. Each of the upper and lower jaw assemblies 18 and 20 includes an elongate jaw body 60a, 60b, respectively and a distal clamping portion 62a, 62b, respectively. The distal clamping portion 62a, 62b of each of the upper and lower jaw assemblies 18 and 20 can be integrally formed with the elongate jaw body 60a, 60b or, as shown in FIG. 4, can be formed separately from the elongated jaw body 60a, 60b and subsequently attached thereto using any known fastening technique including welding.

Each of the elongate jaw bodies 60a, 60b includes a proximal portion 61a, 61b and a central cam portion 80a, 80b. The proximal portion 61a, 61b is positioned within the distal end of the actuator body 26 and defines a through bore 66. The proximal portion 61a, 61b of each of the elongate jaw bodies 60a, 60b is pivotally secured to the distal end of the actuator body 26 by a pivot pin 70 (FIG. 4) that extends through openings 72 in the distal portion of the actuator body 26 and through the through bores 66 in the proximal end of the elongate jaw bodies 60a, 60b of the upper and lower jaw assemblies 18 and 20. The central cam portion 80a of the upper jaw assembly 18 includes a cam slot 82 that diverges outwardly in the distal direction from the longitudinal axis "X". In contrast, the central cam portion 80b of the lower jaw assembly 20 includes a cam slot 84 that diverges inwardly from the longitudinal axis "X" in the distal direction.

The distal end of the elongated body 16 supports a bushing 86 that encloses the distal end of the elongated body 16 and defines a transverse slot 88. The bushing 86 supports a pin or cam member 90. The elongate jaw bodies 60a, 60b of the upper and lower jaw assemblies 18 and 20 extend through the transverse slot 88 of the bushing 86 such that the cam member 90 is received within the cam slots 82 and 84 of the central cam portions 80a and 80b of the elongate jaw bodies 60a, 60b of the upper and lower jaw assemblies 18 and 20. Due to the configuration of the cam slots 82 and 84, distal movement of the upper jaw assembly 18 in relation to the cam member 90 causes the upper jaw assembly 18 move away from the lower jaw assembly 20 and distal movement of the lower jaw assembly 20 in relation to the cam member 90 causes movement of the lower jaw assembly 18 away from the upper jaw assembly 18. Thus, distal movement of the upper and lower jaw assemblies 18, 20 moves the surgical clamping device 10 to an open position. Similarly, proximal movement of the upper jaw assembly 18 in relation to the cam member 90 causes the upper jaw assembly 18 move towards the lower jaw assembly 20 and proximal movement of the lower jaw assembly 20 in relation to the cam member 90 causes movement of the lower jaw assembly 18 towards the upper jaw assembly 18. Thus, proximal movement of the upper and lower jaw assemblies 18, 20 moves the surgical clamping device 10 to a clamped position The distal clamping portion 62a of the upper jaw assembly 18 is secured to a distal end of the elongated jaw body 60a and includes a body 63 having a tissue engaging surface 92 (FIG. 2). The distal clamping portion 62b of the lower jaw assembly 20 is secured to a distal end of the elongated body 60b and includes a body 65 having a tissue engaging surface 93. The body 65 defines a hollow 65a that will be described in further detail below. In embodiments, the tissue engaging surface 92 defines slots 94 (FIG. 2) that open onto the tissue engaging surface 92 and the body 63 defines a longitudinally extending recess 96 that supports a sensor 98. The sensor 98 includes projections 100 (FIG. 2) that extend through the slots 94 in the tissue engaging surface 92 to a position adjacent to the tissue engaging surface 92. A spacer 102 is received in the recess 96 of the body 63 of the upper jaw assembly 18 to hold the sensor 98 in a position to engage tissue adjacent the tissue engaging surface 92 of the body 63. The sensor 98 may be coupled to a controller 103 by wires 98a that extend from the sensor 98 through the elongated body 16 and exit the hand grip 12 through an opening 105.

In embodiments, the hollow 65a of the body 65 of the distal clamping portion 62b of the lower jaw assembly 20 receives an inflatable bladder 101. The inflatable bladder 101 communicates with the controller 103 which can be directed to inflate the bladder 101 via a tube or hose 101a to compress tissue between the bladder 101 and the sensor 98. The hose 101a may extend from the inflatable bladder 101 through the elongated body 16 and exit the hand grip 12 through the opening 105.

The sensor 98 and the inflatable bladder 101 can be provided to identify fluid flow within a vessel clamped between the distal clamping portions 62a, 62b of the upper and lower jaw assemblies 18, 20. In some embodiments, the surgical clamping device 10 can be used to measure blood pressure. More specifically, the inflatable bladder 101 can be used to occlude blood flow through a body lumen and the sensor 98 can be used to detect when blood starts to flow again through the body lumen. The controller 103 can be programmed to inflate the bladder 101 and to interpret signals sent from the sensor 98 to determine blood pressure. In embodiments, the controller 103 may include visual or audible indicia to provide an indication of the results to a clinician.

In embodiments, the distal portion of the each of the elongated jaw bodies 60a, 60b includes an extension 104a, 104b, respectively. The extension 104a is hook-shaped and is configured to be received within a recess 106 formed in a proximal portion of the body 63 of the distal clamping portion 62a of the upper jaw assembly 18. The extension 104a can be secured within the recess 106 to the body 63 of the distal clamping portion 62a using any a variety of fastening techniques including welding, press-fitting and the like.

The extension 104b of the elongated jaw body 60b of the lower jaw assembly 20 is received within a slot 108 (FIG. 4) of a body 65 of the distal clamping portion 62b of the lower jaw assembly 20. As discussed above in regard to the extension 104a, the extension 104b can be secured within the slot 108 of the body 65 of the distal clamping portion 62b using any of a variety of fastening techniques including welding, press-fitting and the like.

FIGS. 1-5 illustrate the surgical clamping device 10 in the clamped position. In the clamped position of the surgical clamping device 10, the actuator assembly 14 is urged to the retracted position by the spring 28 such that the spring 28 is in an uncompressed condition (FIG. 5.) When the actuator assembly 14 is in the retracted position, the upper and lower jaw assemblies 18, 20 are also in a retracted position. More specifically, the actuator body 26 of the actuator assembly 14 is secured to the proximal portions 60a, 60b of the upper and lower jaw assemblies 18, 20 by the pivot pin 70. As such, when the actuator body 26 is in its retracted position, the upper and lower jaw assemblies 18, 20 are in their retracted positions.

Figure 3:
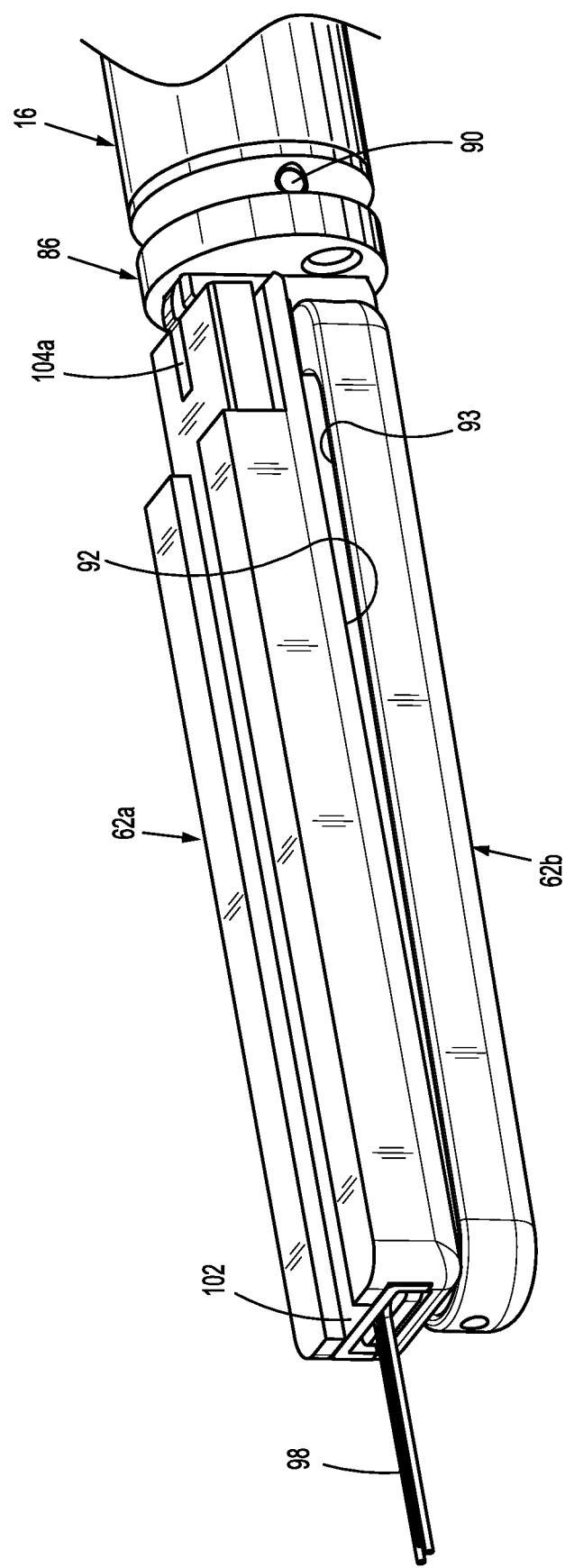
FIG. 3 is an enlarged view of the indicated area of detail shown in FIG. 1.

When the upper and lower jaw assemblies 18, 20 are in their retracted positions, the cam member 90, which is fixedly secured to the bushing 86 at the distal end of the elongated body 16, is positioned in a distal end of the cam slots 82, 84. With the cam member 90 in the distal end of the cam slots 82, 84, the upper and lower jaw assemblies 18, 20 are urged together to the clamped position (FIG. 3).

Figure 6:
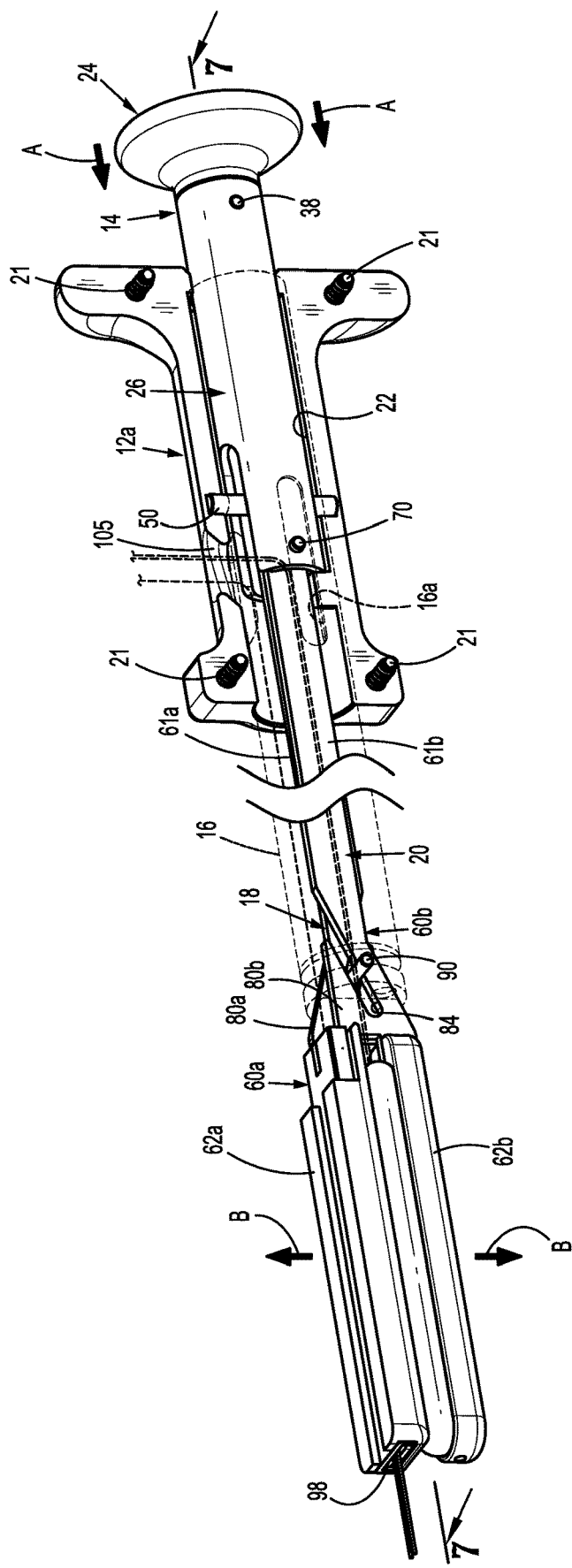
FIG. 6 is side perspective view of the surgical clamping device shown in FIG. 1 with a body portion shown in phantom, a half-section of a handgrip removed, and the jaws moved to an partially closed position.
Figure 11:
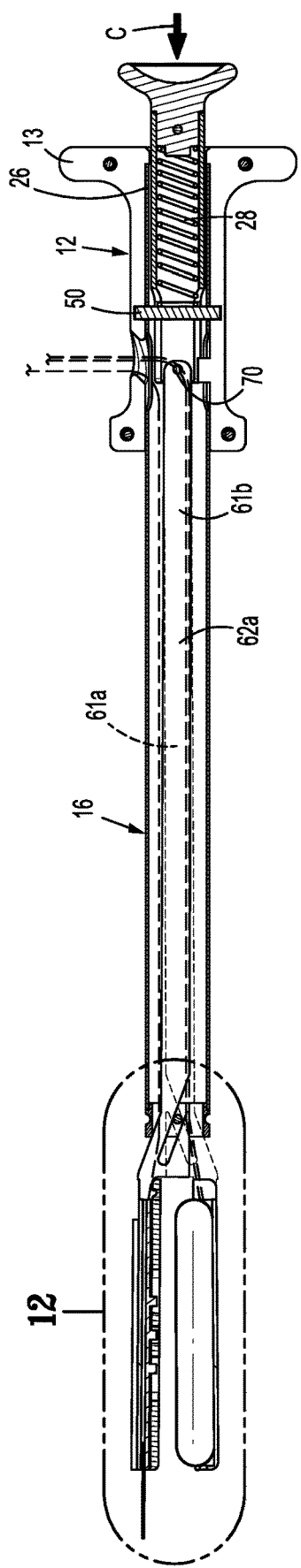
FIG. 11 is a side cross-sectional view taken along section line 11-11 of FIG. 9.
Figure 12:
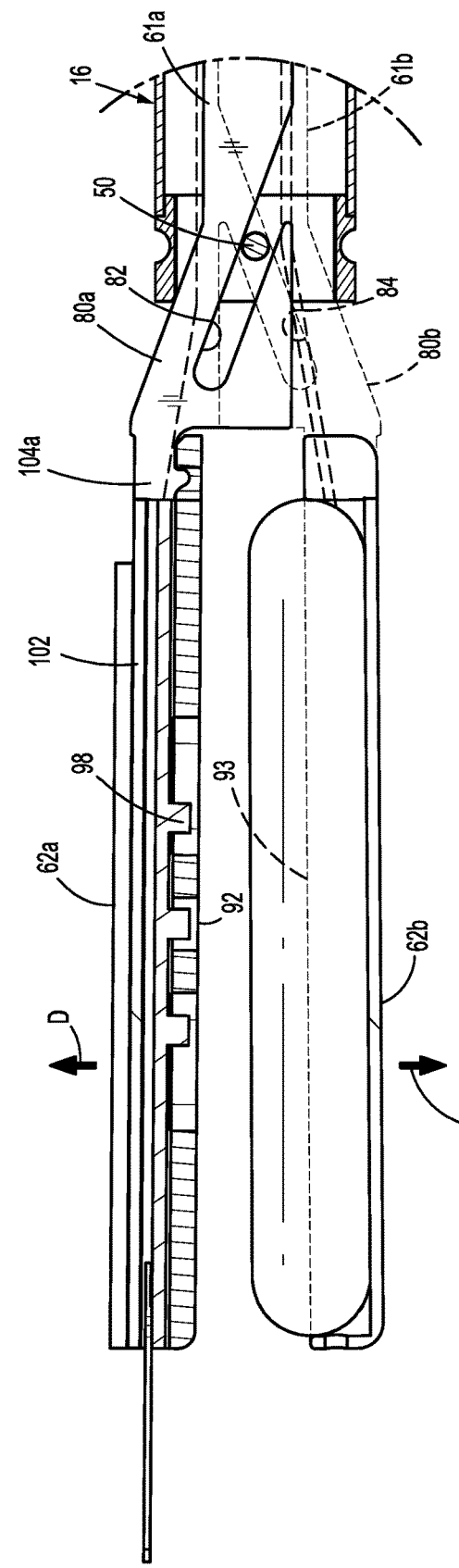
FIG. 12 is an enlarged view of the indicated area of detail shown in FIG. 9.

FIGS. 6-8 illustrate the surgical clamping device 10 as the device 10 is moved from the clamped position (FIG. 1) towards the open position. In order to move the surgical clamping device 10 to the open position, the actuator assembly 14 is pressed distally in relation to the hand grip 12 against the bias of the spring 28 in the direction indicated by arrows "A" in FIGS. 6 and 7. This can be accomplished by a clinician by placing the actuator knob 24 in a palm of a hand, grasping the proximal portion 13 of the hand grip 12 with fingers, and pushing the actuator assembly 14 distally through the hand grip 12. As the actuator assembly 14 moves distally through the hand grip 12, the upper and lower jaw assemblies 18, 20 are advanced distally through the elongated body 16 such that the central cam portions 80a, 80b are moved proximally in relation to the cam member 90, which is stationary, such that the cam member moves towards the proximal end of the cam slots 82, 84 of the upper and lower jaw assemblies 18, 20. As the cam member 90 moves towards the proximal end of the cam slots 82, 84, the upper and lower jaw assemblies 18, 20 are pivoted away from each other in the direction indicated by arrow "B" about the pivot member 70 as the cam member 90 engages the walls defining the cam slots 82, 84.

As shown, the pivot member 70 is positioned in a proximal portion of the surgical clamping device 10 within the hand grip 12 at a distance "d1" (FIG. 7) from a proximal end of the distal clamping portions 62a, 62b. In embodiments, "d1" is between about 4.5 inches and about 7.5 inches. In certain embodiments, "d1" is about 6 inches. Because of the large spacing "d1" between the pivot member 70 and the distal clamping portions 62a, 62b, the distal clamping portions 62a, 62b of the upper and lower jaw assemblies 18, 20 remain substantially parallel to each other as the surgical clamping device 10 moves between the open and clamped positions.

FIGS. 9-12 illustrate the surgical clamping device 10 as the device 10 is moved to the fully open position. In order to move the surgical clamping device 10 to the fully open position, the actuator assembly 14 is pressed to its distal most position within the hand grip 12 against the bias of spring 28 (FIG. 11) in the direction indicated by arrows "C" in FIGS. 9 and 11. As the actuator assembly 14 moves distally through the hand grip 12, the upper and lower jaw assemblies 18, 20 move through the elongated body 16 to their distal most positions such that the cam member 90 is positioned in the proximal end of the cam slots 82, 84 of the upper and lower jaw assemblies 18, 20. As the upper and lower jaw assemblies 18, 20 are moved to their advanced or distal-most positions, the cam member 90 is moved to the proximal end of the cam slots 82, 84. As the cam member 90 engages the walls defining the cam slots 82, 84 of the upper and lower jaw assemblies 18, 20, the upper and lower jaw assemblies are pivoted in the direction indicated by arrow "D" about the pivot member 70 to the fully open position.

As discussed above, the pivot member 70 is spaced from the proximal end of the distal clamping portions 62 of the upper and lower jaw assemblies 18, 20 over an extended distance "d1" (FIG. 7). Because of the large spacing between the distal clamping portions 62a, 62b of the upper and lower jaw assemblies 18, 20 and the pivot member 70, the distal clamping portions 62a, 62b of the upper jaw assembly 18 and the lower jaw assembly 20 remain substantially parallel to each other during movement between open and clamped positions.

FIGS. 13-20 illustrate an alternate embodiment of the presently disclosed surgical stapling device shown generally as 100. The surgical stapling device 100 includes upper and lower jaw assemblies 118 and 120, respectively, and elongated actuator body 174 of the presently disclosed surgical clamping device. Although the surgical stapling device 100 is not shown to include a hand grip, a spring biased actuator assembly, or elongated body as described above in regard to surgical clamping device 10, it is envisioned that the hand grip, actuator assembly, and elongated body such as shown in FIG. 1 could be used in association with the jaw assemblies 118, 120 and the elongated actuator body 174. Surgical clamping device 100 is similar to surgical clamping device 10 in most respects. However, in surgical clamping device 10, the upper and lower jaw assemblies 18, 20 are movable in relation to the cam member 90 and the hand grip 12. In contrast, in the surgical clamping device 100, the upper and lower jaw assemblies 160a, 160b are fixed in relation to the hand grip (not shown) and cam members 190a, 190b are moved in relation to the upper and lower jaw assemblies 160a, 160b as described in further detail below.

Figure 15:
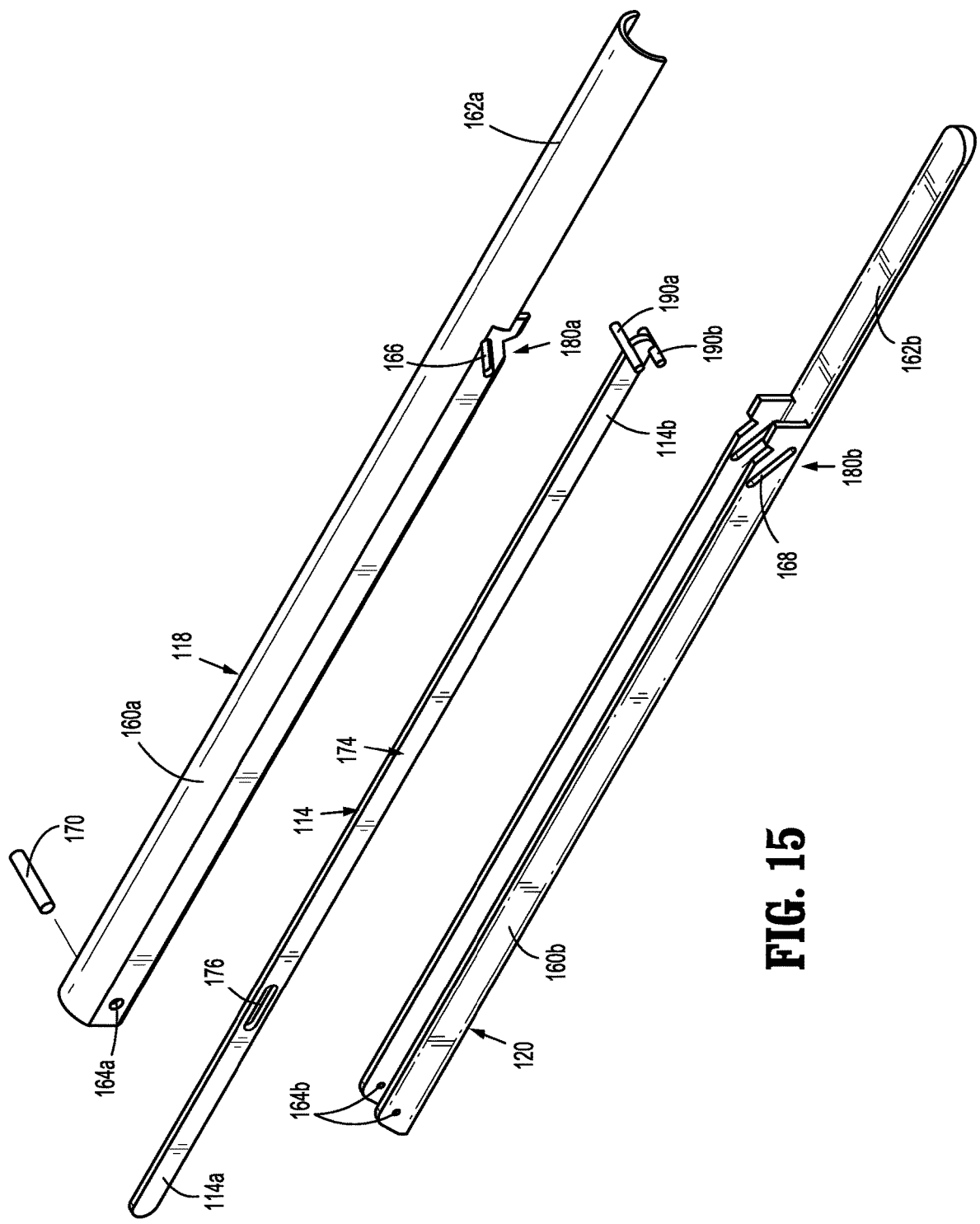
FIG. 15 is a side perspective exploded view of the jaws and actuator shown in FIG. 13.
Figures 21, 22:
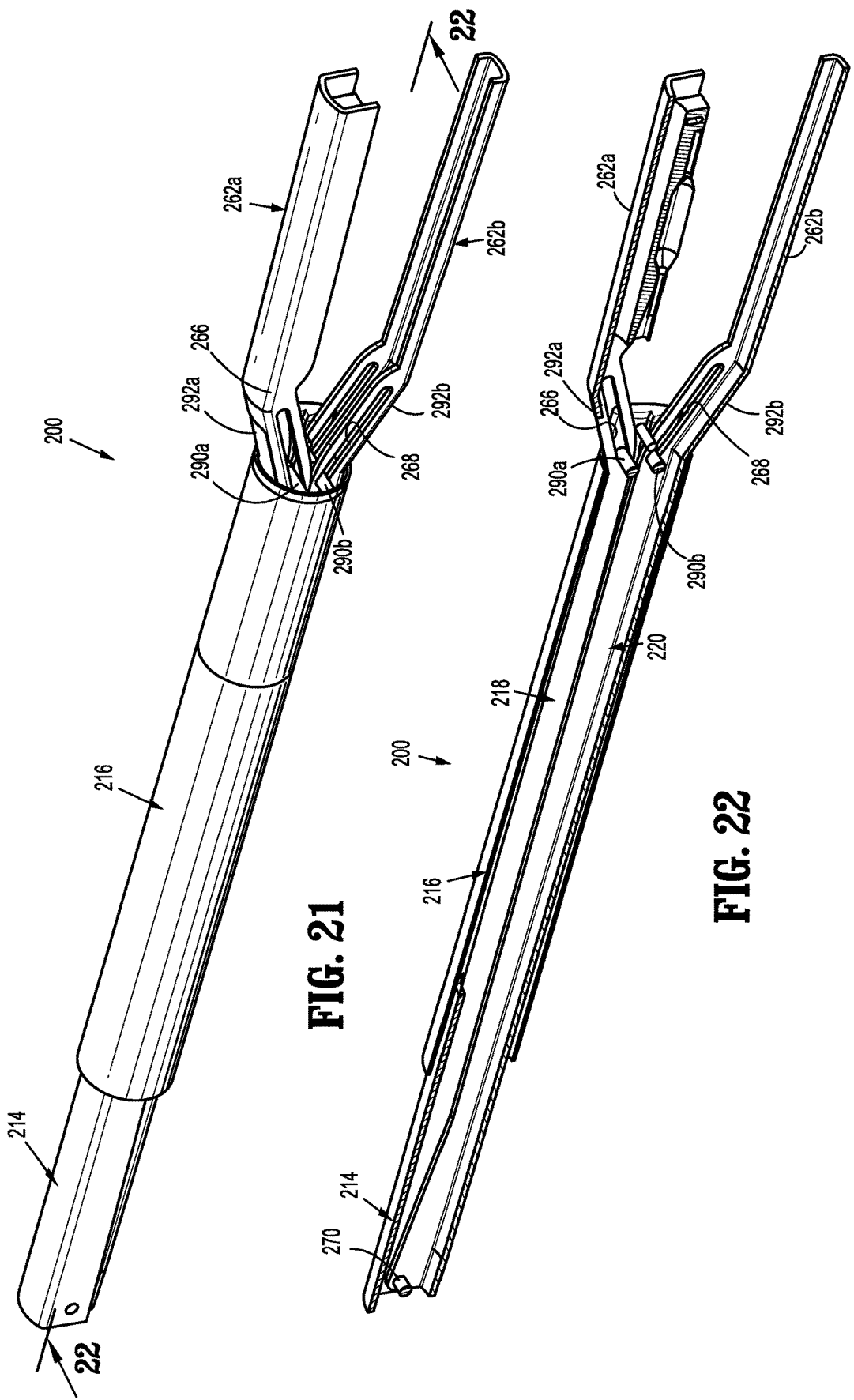
FIG. 21 is a side perspective view of yet another embodiment of the jaws and actuator of the presently disclosed surgical clamping device shown in FIG. 1 with the jaws in the open position.
FIG. 22 is a cross-sectional view taken along section lines 22-22 of FIG. 21.

Referring to FIGS. 13-15, the upper jaw assembly 118 includes an elongated jaw body 160a, a distal clamping portion 162a, and a central cam portion 180a. Similarly, the lower jaw assembly 120 includes an elongated jaw body 160b, a distal clamping portion 162b, and a central cam portion 180b. Each of the elongated jaw bodies 160a, 160b is substantially U-shaped and includes a proximal portion that defines a pair of bores 164a, 164b, respectively. The bores 164a, 164b receive a pivot member 170 to pivotally secure a proximal end of the upper jaw assembly 118 to the proximal end of the lower jaw assembly 120. Although not shown, the pivot member 170 is secured to the hand grip and/or elongated body (FIG. 1) of the surgical clamping device 100 to prevent axial movement of the upper and lower jaw assemblies 118, 120 in relation to the elongated body and hand grip. The central cam portion 180a of the upper jaw assembly 118 defines a cam slot 166 and the central cam portion 180b defines a cam slot 168. The cam slots 166 and 168 diverge outwardly from a longitudinal axis "X" of the elongated actuator body 174 in the distal direction. Similar to the surgical clamping device 10, the pivot member 170 is spaced an extended distance "d1" (FIG. 13) from the distal clamping portions 162a, 162b of the upper and lower jaw assemblies 118, 120.

The elongated actuator body 174 has a proximal portion 114a and a distal portion 114b. The proximal portion 114b defines an elongated slot 176 (FIG. 15) that receives the pivot member 170 such that the elongated actuator body 174 is movable in relation to the pivot member 170 and the upper and lower jaw assemblies 118, 120. The distal portion 114b of the elongated actuator body 174 supports the first and second cam members 190a, 190b which are received within the cam slots 166, 168, respectively.

Referring to FIGS. 16 and 17, when the elongated actuator body 174 is in a retracted position, the pivot member 170 is positioned in a distal end of the elongated slot 176 in the actuator body 174 and the cam members 190a, 190b are positioned in the proximal end of the cam slots 166, 168, respectively, such that the distal clamping portions 162a, 162b of the upper and lower jaw assemblies 118, 120 are in an open position.

Referring to FIGS. 18-20, when the elongated actuator body 174 is advanced in relation to the upper and lower jaw assemblies 118, 120 in the direction indicated by arrow "E", the elongated actuator body 174 moves in relation to the upper and lower jaw assemblies 118, 120 about the pivot member 170 to move the first and second cam members 190a, 190a from the proximal end of the cam slots 166, 168 to the distal end of the cam slots 166, 168. As the cam members 190a, 190b move through the cam slots 166, 168, respectively, the cam members 190a, 190b engage internal walls defining the cam slots 166, 168 to urge the distal clamping portions 162a, 162b of the upper and lower jaw assemblies 118, 120 in the direction indicated by arrow "F" in FIG. 18 to the clamped position.

In embodiments, the elongated actuator body 174 is biased to the advanced position such that the surgical clamping device 100 is normally in a clamped position. Alternately, the elongated actuator body 174 can be biased to the retracted position such that the surgical clamping device 100 is normally in the open position.

As discussed above, the pivot member 170 is spaced from the proximal end of the distal clamping portions 162a, 162b of the upper and lower jaw assemblies 118, 120 an extended distance "d1" (FIG. 18). Because of the large spacing between the proximal end of the distal clamping portions 162a, 162b and the pivot member 170, the distal clamping portions 162a, 162b of the upper jaw assembly 118 and the lower jaw assembly 120 remain substantially parallel to each other during movement of the surgical clamping device 100 between the open and clamped positions.

FIGS. 21-24 illustrate an alternate embodiment of the presently disclosed surgical clamping device shown generally as 200. The surgical clamping device 200 includes upper and lower jaw assemblies 218 and 220, respectively, and an elongated body 216. Although FIGS. 13-20 do not illustrate a hand grip or spring biased actuator assembly as described above in regard to surgical clamping device 10, it is envisioned that the hand grip and actuator assembly such as shown in FIG. 1 could be used in association with the jaw assemblies 218, 220 and elongated body 216. Surgical clamping device 200 is similar to surgical clamping device 10 in most respects. However, in surgical clamping device 10, the cam member 90 is supported on a bushing 86 (FIG. 4). In contrast, in the surgical clamping device 200, cam members 290a, 290b are supported within an elongated body 216 of the surgical clamping device 200 as described in further detail below.

The surgical clamping device 200 includes the elongated body 216 and upper and lower jaw assemblies 218, 220. A proximal portion of the upper and lower jaw assemblies 218, 220 is pivotally secured to an actuator assembly 214 positioned within a hand grip (not shown) about a pivot member 270. The actuator assembly 214 is movable in relation to the elongated body 216 to move the upper and lower jaw assemblies 218, 220 in relation to the elongated body 216. As shown, the cam members 290a, 290b are supported within a distal portion of the elongated body 216 and are movable within cam slots 266, 268 of the upper and lower jaw assemblies 218, 220 as the actuator assembly 214 is moved in relation to the elongated body 216 to pivot the upper and lower jaw assemblies 218, 220 about the pivot member 270 between the open and clamped positions. More specifically, as the upper and lower jaw assemblies 218, 220 are moved in relation to the elongated body 216 in the direction indicated by arrow "G" in FIGS. 23 and 24, the cam members 290a, 290b are moved distally within the cam slots 266, 268 in the direction indicated by arrows "H" in FIGS. 23 and 24 to move the upper and lower jaw assemblies 218, 220 in relation to each other between the open and clamped positions as indicated by arrows. In addition, the distal end of the elongated body 216 also engages cam surfaces 292a, 292b on the distal clamping portions 262a, 262b of the upper and lower jaw assemblies 218, 220 when the upper and lower jaw assemblies are moved in relation to the elongated body 216 to urge the upper and lower jaw assemblies 218, 220 from the open position to the clamped position.

As discussed above, the pivot member 270 is spaced from the proximal end of the distal clamping portions 262a, 262b of the upper and lower jaw assemblies 218, 220 an extended distance "d1" (FIG. 18). Because of the large spacing between the proximal end of the distal clamping portions 262a, 262b and the pivot member 270, the distal clamping portions 262a, 262b of the upper jaw assembly 218 and the lower jaw assembly 220 remain substantially parallel to each other during movement of the surgical clamping device 200 between the open and clamped positions.

The surgical clamping device 300 shown in FIGS. 25-28 is substantially similar to the surgical clamping device 200 of FIGS. 21-24 but does not include the cam members 290a, 290b. More specifically, the surgical clamping device 300 includes an elongated body 316 and upper and lower jaw assemblies 318, 320. A proximal portion of the upper and lower jaw assemblies 318, 320 is pivotally secured to a portion of the actuator assembly 314 by a pivot member 370. The actuator assembly 314 is movable in relation to the elongated body 316 to move the upper and lower jaw assemblies 318, 320 into or out of a distal end of the elongated body 316. As the upper and lower jaw assemblies move into and out of the distal end of the elongated body 316, engagement between the distal end of the elongate body 316 and cam surfaces 392a, 392b of the upper and lower jaw assemblies 318, 320 pivots the upper and lower jaw assemblies 318, 320 between the open and clamped positions.

As discussed above, the pivot member 370 is spaced from the proximal end of the distal clamping portions 362a, 362b of the upper and lower jaw assemblies 318, 320 an extended distance "d1" (FIG. 18). Because of the large spacing between the proximal end of the distal clamping portions 362a, 362b and the pivot member 370, the distal clamping portions 362a, 362b of the upper jaw assembly 318 and the lower jaw assembly 320 remain substantially parallel to each other during movement of the surgical clamping device 300 between the open and clamped positions.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical clamping device comprising:
  a hand grip;
  an actuator assembly supported by the hand grip, the actuator assembly being movable in relation to the hand grip between retracted and advanced positions;
  an elongated body supported on and extending distally from the hand grip, the elongated body defining a longitudinal axis and supporting a cam member; and
  upper and lower jaw assemblies, each of the upper and lower jaw assemblies including an elongate jaw body and a distal clamping portion, each of the distal clamping portions including a cam surface, each of the elongate jaw bodies extending from the hand grip through the elongated body and including a proximal portion pivotally secured to the actuator assembly within the hand grip about a pivot member, wherein the actuator is movable between a retracted position and an advanced position to move the cam surfaces of the distal clamping portions in relation to the cam member of the elongated body to pivot the upper and lower jaw assemblies in relation to each other between an open position and a clamped position.

2. The surgical clamping device of claim 1, wherein the actuator assembly includes a biasing member positioned to urge the upper and lower jaw assemblies to the clamped position.

3. The surgical clamping device of claim 1, further including a bushing supported on a distal end of the elongated body, the bushing defining a transverse slot and supporting the cam member, the upper and lower jaw assemblies extending through the transverse slot.

4. The surgical clamping device of claim 1, wherein each of the upper and lower jaw assemblies includes a central cam portion that defines a cam slot, the cam member being received within the cam slots of the upper and lower jaw assemblies.

5. The surgical clamping device of claim 4, wherein the cam member includes first and second cam members, each of the first and second cam members being positioned within one of the cam slots of the upper and lower jaw assemblies.

6. The surgical clamping device of claim 1, further including a fluid flow sensor supported on one of the upper and lower jaw assemblies, the fluid flow sensor being provided to identify fluid flow within a vessel clamped between the distal clamping portions of the upper and lower jaw assemblies.

7. The surgical clamping device of claim 6, wherein the other one of the upper and lower jaw supports an inflatable bladder, wherein the inflatable bladder and the sensor are positioned such that in the clamped position tissue is clamped between the sensor and the inflatable bladder.

8. The surgical clamping device of claim 1, wherein the upper and lower jaw assemblies are axially movable in relation to the elongated body.

9. The surgical clamping device of claim 1, wherein the upper and lower jaw assemblies are axially fixed in relation to the elongated body.

10. The surgical clamping device of claim 1, wherein the hand grip defines a through bore and the actuator assembly is movably supported within the through bore.

11. The surgical clamping device of claim 1, wherein the actuator assembly includes an actuator knob, an actuator body, and a biasing member, the actuator knob being supported on a proximal portion of the actuator body and extending from a proximal end of the hand grip.

12. The surgical clamping device of claim 11, wherein the actuator body is tubular and the biasing member includes a coil spring positioned within the actuator body.

13. The surgical clamping device of claim 12, further including a cross-pin fixedly supported within the through bore of the hand grip, the cross-pin extending through the actuator body and engaging a distal end of the coil spring.

14. The surgical clamping device of claim 13, wherein the actuator body defines spaced longitudinally extending cut outs, the cross-pin being positioned within the longitudinally extending cut outs such that the actuator body is axially moveable in relation to the hand grip and the cross-pin.

15. The surgical clamping device of claim 1, wherein the pivot member is spaced from a proximal end of the distal clamping portions by a distance d1, wherein d1 is greater than 4.5 inches.

16. The surgical clamping device of claim 1, wherein the pivot member is spaced from a proximal end of the distal clamping portions by a distance d1, wherein d1 is between 4.5 inches and 7.5 inches.

17. The surgical clamping device of claim 1, wherein the pivot member is spaced from a proximal end of the distal clamping portions by a distance d1, wherein d1 is 6 inches.

18. The surgical clamping device of claim 1, wherein each of the upper and lower jaw assemblies includes a central cam portion that defines an outer cam surface, the outer cam surfaces being positioned to engage a distal end of the elongated body to effect movement of the upper and lower jaw assemblies towards the clamped position.

19. The surgical clamping device of claim 18, further including a controller, the controller being configured to facilitate inflation of the inflatable bladder and actuation of the sensor.

\* \* \* \* \*